United States Patent
Davis et al.

(10) Patent No.: US 9,597,198 B2
(45) Date of Patent: Mar. 21, 2017

(54) TRANSFORAMINAL INTERSOMATIC CAGE FOR AN INTERVERTEBRAL FUSION GRAFT AND AN INSTRUMENT FOR IMPLANTING THE CAGE

(71) Applicant: LDR Medical, Rosieres Pres Troyes (FR)

(72) Inventors: Reginald James Davis, Cockeysville, MD (US); Kevin Kaufman, Fort Worth, TX (US); Greg Hoffman, Fort Wayne, IN (US); Alan McGee, Fort Wayne, IN (US); Jean Huppert, L'Etrat (FR); Hugues Mousselard, Paris (FR); Ludovic Rillardon, Le Raincy (FR)

(73) Assignee: LDR Medical, Sainte-Savine (FR)

( * ) Notice: Subject to any disclaimer, the term of this patent is extended or adjusted under 35 U.S.C. 154(b) by 0 days.

(21) Appl. No.: 13/854,808

(22) Filed: Apr. 1, 2013

(65) Prior Publication Data
US 2014/0135932 A1    May 15, 2014

Related U.S. Application Data

(63) Continuation of application No. 11/378,165, filed on Mar. 17, 2006, now Pat. No. 8,409,288.

(30) Foreign Application Priority Data

Feb. 15, 2006 (FR) ..................................... 06 01315

(51) Int. Cl.
*A61F 2/44* (2006.01)
*A61F 2/46* (2006.01)
(Continued)

(52) U.S. Cl.
CPC .......... *A61F 2/4455* (2013.01); *A61F 2/4611* (2013.01); *A61F 2002/2835* (2013.01);
(Continued)

(58) Field of Classification Search
CPC ................................ A61F 2/46; A61F 2/4465
(Continued)

(56) References Cited

U.S. PATENT DOCUMENTS 3,867,728 A    2/1975 Stubstad et al.
4,820,305 A    4/1989 Harms et al.
(Continued)

FOREIGN PATENT DOCUMENTS

DE    4323034    7/1994
DE    4315757    11/1994
(Continued)

OTHER PUBLICATIONS

Japan Patent Office; Office Action for Pub'n No. JP2009532075, Application No. JP20080554874; Nov. 4, 2011; Japan Patent Office; Tokyo, Japan; all pages.
(Continued)

Primary Examiner — Jan Christopher Merene
(74) Attorney, Agent, or Firm — Lauff Law PLLC

(57) ABSTRACT

This present invention concerns a transforaminal intersomatic cage for an intervertebral fusion graft, and an instrument and method for implanting the cage, an embodiment of the cage having a body in the shape of a circular arc and comprising a lateral concave surface, a lateral convex surface, a straight upper surface, a straight lower surface and an end wall having at least one hole, called the end hole, designed to receive a rod of an instrument for implanting the cage between the vertebrae, wherein: the end hole has an orientation that is more or less tangential to the circular arc described by the body; the extremity opposite the end wall
(Continued)

of the body includes a return part extending the body toward the center of the circle on which the circular arc described by the body lies.

20 Claims, 4 Drawing Sheets

(51) Int. Cl.
  *A61F 2/28* (2006.01)
  *A61F 2/30* (2006.01)
(52) U.S. Cl.
  CPC .......... *A61F 2002/3008* (2013.01); *A61F 2002/30131* (2013.01); *A61F 2002/30192* (2013.01); *A61F 2002/30308* (2013.01); *A61F 2002/30576* (2013.01); *A61F 2002/30579* (2013.01); *A61F 2002/30594* (2013.01); *A61F 2002/30795* (2013.01); *A61F 2002/30845* (2013.01); *A61F 2002/30879* (2013.01); *A61F 2002/30884* (2013.01); *A61F 2002/30892* (2013.01); *A61F 2002/30894* (2013.01); *A61F 2002/4627* (2013.01); *A61F 2230/0013* (2013.01); *A61F 2230/0041* (2013.01); *A61F 2230/0063* (2013.01); *A61F 2250/0098* (2013.01)
(58) Field of Classification Search
  USPC .............. 606/99, 279; 623/17.11, 17.16
  See application file for complete search history.

(56) References Cited

U.S. PATENT DOCUMENTS

| | | | |
|---|---|---|---|
| 4,892,545 A | 1/1990 | Day et al. | |
| 4,917,704 A | 4/1990 | Frey et al. | |
| 4,919,667 A | 4/1990 | Richmond | |
| 4,955,908 A | 9/1990 | Frey et al. | |
| 5,071,437 A | 12/1991 | Steffee | |
| 5,320,644 A | 6/1994 | Baumgartner | |
| 5,344,459 A | 9/1994 | Swartz | |
| 5,443,514 A | 8/1995 | Steffee | |
| 5,507,816 A | 4/1996 | Bullivant | |
| 5,534,030 A | 7/1996 | Navarro et al. | |
| 5,545,229 A | 8/1996 | Parsons et al. | |
| 5,683,463 A | 11/1997 | Godefroy et al. | |
| 5,861,041 A | 1/1999 | Tienboon | |
| 5,897,556 A | 4/1999 | Drewry et al. | |
| 6,039,762 A | 3/2000 | McKay | |
| 6,059,829 A | 5/2000 | Schlapfer et al. | |
| 6,241,771 B1 | 6/2001 | Gresser et al. | |
| 6,540,753 B2 | 4/2003 | Cohen | |
| 6,558,424 B2 | 5/2003 | Thalgott | |
| 7,235,082 B2 * | 6/2007 | Bartish et al. | 606/99 |
| 7,611,538 B2 | 11/2009 | Belliard et al. | |
| 7,637,953 B2 * | 12/2009 | Branch et al. | 623/17.11 |
| 7,744,602 B2 * | 6/2010 | Teeny et al. | 606/99 |
| 7,905,886 B1 * | 3/2011 | Curran et al. | 606/99 |
| 7,998,211 B2 | 8/2011 | Baccelli et al. | |
| 8,241,359 B2 * | 8/2012 | Davis et al. | 623/17.11 |
| 8,267,999 B2 | 9/2012 | Beaurain et al. | |
| 8,313,528 B1 | 11/2012 | Wensel | |
| 8,343,219 B2 | 1/2013 | Allain et al. | |
| 8,349,015 B2 | 1/2013 | Bae et al. | |
| 8,696,681 B2 * | 4/2014 | Harris et al. | 606/99 |
| 2002/0070565 A1 | 6/2002 | Szapucki et al. | |
| 2002/0087212 A1 | 7/2002 | James et al. | |
| 2002/0165613 A1 | 11/2002 | Lin et al. | |
| 2004/0210227 A1 | 10/2004 | Trail et al. | |
| 2005/0177236 A1 | 8/2005 | Mathieu et al. | |
| 2006/0121084 A1 | 6/2006 | Borden et al. | |
| 2006/0142863 A1 | 6/2006 | Fraser et al. | |
| 2006/0235426 A1 * | 10/2006 | Lim et al. | 606/99 |
| 2006/0241761 A1 * | 10/2006 | Gately | 623/17.11 |
| 2007/0093850 A1 * | 4/2007 | Harris et al. | 606/99 |
| 2007/0142843 A1 * | 6/2007 | Dye | 606/99 |
| 2007/0162128 A1 * | 7/2007 | DeRidder et al. | 623/17.11 |
| 2010/0280618 A1 | 11/2010 | Jodaitis et al. | |
| 2013/0150968 A1 | 6/2013 | Dinville et al. | |
| 2013/0166029 A1 | 6/2013 | Dinville et al. | |

FOREIGN PATENT DOCUMENTS

| | | |
|---|---|---|
| DE | 4318700 | 11/1994 |
| DE | 4423826 | 1/1995 |
| DE | 9413778 | 1/1996 |
| DE | 19504867 | 2/1996 |
| DE | 19615938 | 10/1996 |
| EP | 0179695 | 4/1986 |
| EP | 0346129 | 12/1989 |
| EP | 0356112 | 2/1990 |
| EP | 0392076 | 10/1990 |
| EP | 0298235 | 12/1991 |
| EP | 0538183 | 4/1993 |
| EP | 0599419 | 6/1994 |
| EP | 0630625 | 12/1994 |
| EP | 0662309 | 7/1995 |
| EP | 0637440 | 10/1997 |
| FR | 2710519 | 4/1995 |
| FR | 2724312 | 3/1996 |
| FR | 2736537 | 1/1997 |
| FR | 2987256 | 8/2013 |
| FR | 3005569 | 11/2014 |
| FR | 3016793 | 7/2015 |
| JP | H03505416 | 11/1991 |
| JP | H06285099 | 10/1994 |
| JP | H08503876 | 4/1996 |
| JP | H09503416 | 4/1997 |
| JP | H09122160 | 5/1997 |
| JP | H11506658 | 6/1999 |
| JP | H11513601 | 11/1999 |
| JP | 2001507243 | 6/2001 |
| RU | 2177278 | 12/2001 |
| WO | WO9011740 | 10/1990 |
| WO | WO9310725 | 6/1993 |
| WO | WO9507668 | 3/1995 |
| WO | WO9617564 | 6/1996 |
| WO | WO9627348 | 9/1996 |
| WO | WO9640014 | 12/1996 |
| WO | WO9706753 | 2/1997 |
| WO | WO9715247 | 5/1997 |
| WO | WO9723175 | 7/1997 |
| WO | WO2013124453 | 8/2013 |
| WO | WO2014184367 | 11/2014 |
| WO | WO2015114122 | 8/2015 |

OTHER PUBLICATIONS

LDR Medical, by its attorneys; Written Argument and Written Amendment for Pub'n No. JP2009532075, Application No. JP20080554874; May 15, 2012; Japan Patent Office; Tokyo, Japan; all pages.
LDR Medical, by its attorneys; Reply to Office Action in U.S. Appl. No. 13/585,063; Aug. 11, 2015; USPTO; Alexandria, Virginia; All Pages.
U.S. Patent & Trademark Office; Office Action in U.S. Appl. No. 13/585,063; Nov. 6, 2014; USPTO; Alexandria, Virginia; All Pages.
LDR Medical, by its attorneys; Reply to Office Action in U.S. Appl. No. 13/585,063; Jan. 6, 2015; USPTO; Alexandria, Virginia; All Pages.
U.S. Patent & Trademark Office; Office Action in U.S. Appl. No. 13/585,063; Feb. 11, 2015; USPTO; Alexandria, Virginia; All Pages.
U.S. Patent & Trademark Office; Office Action in U.S. Appl. No. 13/585,063; Nov. 4, 2015; USPTO; Alexandria, Virginia; All Pages.
LDR Medical, by its attorneys; Reply to Office Action in U.S. Appl. No. 13/585,063; Feb. 4, 2016; USPTO; Alexandria, Virginia; All Pages.
LDR Medical, by its attorneys; Reply to Office Action in U.S. Appl. No. 13/585,063; May 4, 2016; USPTO; Alexandria, Virginia; All Pages.

(56) References Cited

OTHER PUBLICATIONS

U.S. Patent & Trademark Office; Office Action in U.S. Appl. No. 13/585,063; Jun. 17, 2016; USPTO; Alexandria, Virgina; All Pages.
National Institute of Industrial Property (France); Search Report for Pub'n. No. FR2808995, App. No. FR0006351; Jan. 29, 2001; National Institute of Industrial Property (France); France; all pages.
World Intellectual Property Organization; International Search Report for International App. No. PCT-FR01-01545, PCT Pub'n. No. WO0187194; Sep. 5, 2001; WIPO; Geneva, Switzerland; all pages.
World Intellectual Property Organization; International Preliminary Examination Report for International App. No. PCT-FR01-01545, PCT Pub'n No. WO0187194; Aug. 30, 2002; WIPO; Geneva, Switzerland; all pages.
U.S. Patent & Trademark Office; Office Action in U.S. Appl. No. 11/767,386; Apr. 24, 2013; USPTO; Alexandria, Virgina; All Pages.
LDR Medical, by its attorneys; Reply to Office Action in U.S. Appl. No. 11/767,386; Jul. 24, 2013; USPTO; Alexandria, Virginia; All Pages.
U.S. Patent & Trademark Office; Notice of Allowance in U.S. Appl. No. 11/767,386; Aug. 30, 2013; USPTO; Alexandria, Virginia; All Pages.
LDR Medical, by its attorneys; Response to Statement of Reasons for Allowance in U.S. Appl. No. 11/767,386; Dec. 2, 2013; USPTO; Alexandria, Virginia; All Pages.
U.S. Patent & Trademark Office; Office Action in U.S. Appl. No. 14/149,357; Jun. 30, 2015; USPTO; Alexandria, Virgina; All Pages.
LDR Medical, by its attorneys; Reply to Office Action in U.S. Appl. No. 14/149,357; Aug. 31, 2015; USPTO; Alexandria, Virginia; All Pages.
U.S. Patent & Trademark Office; Office Action in U.S. Appl. No.14/149,357; Sep. 11, 2015; USPTO; Alexandria, Virgina; All Pages.
LDR Medical, by its attorneys; Reply to Office Action in U.S. Appl. No. 14/149,357; Dec. 11, 2015; USPTO; Alexandria, Virgina; All Pages.
U.S. Patent & Trademark Office; Office Action in U.S. Appl. No. 14/149,357; Feb. 10, 2016; USPTO; Alexandria, Virgina; All Pages.
LDR Medical, by its attorneys; Reply to Office Action in U.S. Appl. No. 14/149,357; May 10, 2016; USPTO; Alexandria, Virgina; All Pages.
U.S. Patent & Trademark Office; Office Action in U.S. Appl. No. 14/149,357; Jun. 1, 2016; USPTO; Alexandria, Virgina; All Pages.
LDR Medical, by its attorneys; CHECK in U.S. Appl. No. 14/149,357; Jun. 8, 2016; USPTO; Alexandria, Virgina; All Pages.
LDR Medical, by its attorneys; Reply to Office Action in U.S. Appl. No. 14/149,357; Jul. 8, 2016; USPTO; Alexandria, Virginia; All Pages.
National Institute of Industrial Property (France); Search Report for Pub'n No. FR2827156, App. No. FR0109381; Apr. 5, 2002; National Institute of Industrial Property (France); France; all pages.
World Intellectual Property Organization; International Search Report for International App. No. PCT/IB02/03390, PCT Pub'n No. WO03005939; Mar. 3, 2003; WIPO; Geneva, Switzerland; all pages.
World Intellectual Property Organization; International Preliminary Examination Report for International App. No. PCT/IB02/03390, PCT Pub'n No. WO03005939; Nov. 6, 2003; WIPO; Geneva, Switzerland; all pages.
U.S Patent & Trademark Office; Office Action in U.S. Appl. No. 13/438,352; Aug. 14, 2014; USPTO; Alexandria, Virgina; All Pages.
LDR Medical, by its attorneys; Reply to Office Action in U.S. Appl. No. 13/438,352; Jan. 14, 2015; USPTO; Alexandria, Virgina; All Pages.
U.S. Patent & Trademark Office; Notice of Allowance in U.S. Appl. No. 13/438,352; Mar. 2, 2015; USPTO; Alexandria, Virgina; All Pages.
U.S. Patent & Trademark Office; Office Action in U.S. Appl. No. 13/732,244; Apr. 30, 2014; USPTO; Alexandria, Virgina; All Pages.

LDR Medical, by its attorneys; Reply to Office Action in U.S. Appl. No. 13/732,244; Jul. 30, 2014; USPTO; Alexandria, Virgina; All Pages.
U.S. Patent & Trademark Office; Office Action in U.S. Appl. No. 13/732,244; Sep. 19, 2014; USPTO; Alexandria, Virginia; All Pages.
LDR Medical, by its attorneys; Reply to Office Action in U.S. Appl. No. 13/732,244; Jan. 20, 2015; USPTO; Alexandria, Virginia; All Pages.
U.S. Patent & Trademark Office; Office Action in U.S. Appl. No. 13/732,244; Feb. 20, 2015; USPTO; Alexandria, Virgina; All Pages.
LDR Medical, by its attorneys; Reply to Office Action in U.S. Appl. No. 13/732,244; Aug. 20, 2015; USPTO; Alexandria, Virginia; All Pages.
U.S. Patent & Trademark Office; Office Action in U.S. Appl. No. 13/732,244; Oct. 20, 2016; USPTO; Alexandria, Virginia; All Pages.
LDR Medical, by its attorneys; Reply to Office Action in U.S. Appl. No. 13/732,244; Jan. 20, 2016; USPTO; Alexandria, Virginia; All Pages.
U.S. Patent & Trademark Office; Office Action in U.S. Appl. No. 13/732,244; Jun. 8, 2016; USPTO; Alexandria, Virginia; All Pages.
LDR Medical, by its attorneys; Amendment for Pub'n No. EP2519194, Application No. EP20090812464; Mar. 25, 2013; EPO; Munich, Germany; all pages.
LDR Medical, by its attorneys; Office Action in Pub'n No. EP2519194, Application No. EP20090812464; Mar. 3, 2016; EPO; Munich, Germany; all pages.
U.S. Patent & Trademark Office; Office Action in U.S. Appl. No. 13/520,041; Mar. 20, 2014; USPTO; Alexandria, Virgina; All Pages.
LDR Medical, by its attorneys; Reply to Office Action in U.S. Appl. No. 13/520,041; Sep. 19, 2014; USPTO; Alexandria, Virgina; All Pages.
U.S. Patent & Trademark Office; Office Action in U.S. Appl. No. 13/520,041; Oct. 6, 2014; USPTO; Alexandria, Virgina; All Pages.
LDR Medical, by its attorneys; Reply to Office Action in U.S. Appl. No. 13/520,041; Mar. 6, 2015; USPTO; Alexandria, Virgina; All Pages.
U.S. Patent & Trademark Office; Office Action in U.S. Appl. No. 13/520,041; Apr. 10, 2015; USPTO; Alexandria, Virgina; All Pages.
LDR Medical, by its attorneys; Reply to Office Action in U.S. Appl. No. 13/520,041; Aug. 10, 2015; USPTO; Alexandria, Virgina; All Pages.
LDR Medical, by its attorneys; Notice of Allowance in U.S. Appl. No. 13/520,041; Nov. 18, 2015; USPTO; Alexandria, Virginia; All Pages.
U.S. Patent & Trademark Office; Notice of Allowance in U.S. Appl. No. 13/520,041; Mar. 8, 2016; USPTO; Alexandria, Virginia; All Pages.
LDR Medical, by its attorneys; Reply to Office Action in U.S. Appl. No. 13/520,041; Jun. 7, 2016; USPTO; Alexandria, Virginia; All Pages.
U.S. Patent & Trademark Office; Office Action in U.S. Appl. No. 13/538,078; May 12, 2014; USPTO; Alexandria, Virginia; All Pages.
LDR Medical, by its attorneys; Reply to Office Action in U.S. Appl. No. 13/538,078; Oct. 14, 2014; USPTO; Alexandria, Virginia; All Pages.
U.S. Patent & Trademark Office; Notice of Allowance in U.S. Appl. No. 13/538,078; Oct. 20, 2014; USPTO; Alexandria, Virginia; All Pages.
U.S. Patent & Trademark Office; Office Action in U.S. Appl. No. 14/726,558; Jun. 22, 2016; USPTO; Alexandria, Virgina; All Pages.
National Institute of Industrial Property (France); Search Report in Fench Pub. No. FR2987256, App. No. FR1251733; Dec. 5, 2012; National Institute of Industrial Property (France); France; all pages.
World Intellectual Property Organization; International Search Report and Written Opinion of the International Searching Authority for International App. No. PCT/EP2013/053622, PCT Pub'n No. WO2013124453; May 29, 2013; WIPO; Geneva, Switzerland; all pages.

(56) References Cited

OTHER PUBLICATIONS

LDR Medical, by its attorneys; Response to International Search Report for International App. No. PCT/EP2013/053622, PCT Pub'n No. WO 2013/124453; Dec. 18, 2013; Wipo; Geneva, Switzerland; all pages.
World Intellectual Property Organization; International Preliminary Report on Patentability for International App. No. PCT/EP2013/053622, PCT Pub'n No. WO 2013/124453; Jul. 11, 2014; WIPO; Geneva, Switzerland; all pages.
U.S. Patent & Trademark Office; Notice of Allowance in U.S. Appl. No. 13/774,547; Jul. 3, 2014; USPTO; Alexandria, Virgina; All Pages.
U.S. Patent & Trademark Office; Examiner's Interview Summary in U.S. Appl. No. 13/774,547; Jul. 3, 2014; USPTO; Alexandria, Virginia; All Pages.
U.S. Patent & Trademark Office; Notice of Allowance in U.S. Appl. No. 13/774,547; Oct. 16, 2014; USPTO; Alexandria, Virginia; All Pages.
LDR Medical, by its attorneys; Reply to Office Action in U.S. Appl. No. 13/774,547; Feb. 2, 2015; USPTO; Alexandria, Virginia; All Pages.
U.S. Patent & Trademark Office; Notice of Allowance in U.S. Appl. No. 13/774,547; Feb. 2, 2015; USPTO; Alexandria, Virginia; All Pages.
U.S. Patent & Trademark Office; Office Action in U.S. Appl. No. 14/721,818; Sep. 24, 2015; USPTO; Alexandria, Virginia; All Pages.
LDR Medical, by its attorneys; Reply to Office Action in U.S. Appl. No. 14/721,818; Dec. 28, 2015; USPTO; Alexandria, Virginia; All Pages.
U.S. Patent & Trademark Office; Office Action in U.S. Appl. No. 14/721,818; Feb. 1, 2016; USPTO; Alexandria, Virgina; All Pages.
LDR Medical, by its attorneys; CHECK in U.S. Appl. No. 14/721,818; May 2, 2016; USPTO; Alexandria, Virgina; All Pages.
U.S. Patent & Trademark Office; Office Action in U.S. Appl. No. 14/721,818; Jun. 1, 2016; USPTO; Alexandria, Virgina; All Pages.
World Intellectual Property Organization; International Search Report for International App. No. WO2014184367, PCT Pub'n No. PCT/EP2014/060135; Aug. 26, 2014; WIPO; Geneva, Switzerland; all pages.
National Institute of Industrial Property (France); Search Report in Fench Pub. No. FR3016793, App. No. FR1450749; Sep. 11, 2014; National Institute of Industrial Property (France); France; all pages.
World Intellectual Property Organization; International Search Report and Written Opinion of the International Searching Authority for International App. No. WO2015114122, PCT Pub'n No. PCT/EP2015/052019; May 13, 2015; WIPO; Geneva, Switzerland; all pages.

\* cited by examiner

TRANSFORAMINAL INTERSOMATIC CAGE FOR AN INTERVERTEBRAL FUSION GRAFT AND AN INSTRUMENT FOR IMPLANTING THE CAGE

CROSS REFERENCE TO RELATED APPLICATIONS

This application is a divisional of U.S. patent application Ser. No. 11/378,165 filed Mar. 17, 2006, and issuing as U.S. Pat. No. 8,409,288 on Apr. 2, 2013, which claims priority under 35 U.S.C. 119 to French Patent Application No. FR0601315, filed in FRANCE on Feb. 15, 2006, both of which are incorporated herein by reference for all purposes.

BACKGROUND

This present invention concerns the area of intervertebral arthrodeses (fusion of two vertebrae) and in particular of intersomatic cages implanted between two adjacent vertebrae to allow the insertion and the growth of grafts of osseous tissue (or of substitute) in the disc space. In fact, after the insertion of the cage or implant, the intervertebral space is filled with autologous spongy bone or suitable bone substitutes. The invention also concerns an instrument for implanting the cage between the vertebrae, in particular through the transforaminal approach. The intersomatic cages are designed to be positioned between two vertebrae, in order to restore and/or maintain the disc space by replacing the intervertebral disc, and the grafts of osseous tissue or of substitute are designed to allow fusion between the two adjacent vertebrae between which they are inserted.

Various types of intersomatic cage are known from prior art. Some intersomatic cages known from prior art are machined from bone, most often cortical bone, so as to fuse with the graft inserted into the disc space. These cages composed of bone have the disadvantage to being capable of causing illness in the event of imperfect sterilisation.

Different intersomatic cages in solid materials of various types are also known from prior art. These cages include openings on their lower surface, their upper surface and on at least one of their lateral surfaces. One of these cages, in particular known from patent application WO0187194 (A1) submitted by the present applicant, has the shape of an open ring and can be used in combination with another cage of the same type by placing the open lateral surfaces of the two cages opposite to each other. Whatever the type of cage in question, spongy bone is compacted inside the cage, in order to finally achieve an osseous fusion (or arthrodesis) of the two vertebrae separated by a suitable disc space. Other cages known from previous designs are of parallelepiped shape, with the top and the bottom of the cage being completely open, and the top and bottom openings being designed to be positioned facing two vertebrae which have to be kept apart from each other. Openings created in the lateral faces of the parallelepipeds allow the graft to grow toward the exterior of the cage and possibly to reach a graft implanted in another cage also inserted into the disc space. These intersomatic cages have the disadvantage, firstly, of requiring a relatively large incision in the annulus (the outer part of the intervertebral disc), secondly, of requiring a relatively long time before achieving an arthrodesis, because of the confinement of the graft within a chamber at the centre of the cage and, thirdly, of having dimensions that are too large to be implanted through the transforaminal approach without partial or total ablation of the articular processes located posterior to the foramen through which the transforaminal approach runs.

Also known from previous designs in prior art, in particular from American patent application US 2005/0038511 (A1), are intersomatic cages of various shapes and dimensions, machined from bone, and in particular an intersomatic cage of banana (or simple bracket) shape defining a longitudinal axis of the cage and having a lower surface and an upper surface, both straight, equipped with serrations and more or less parallel to the longitudinal axis of the cage, a concave lateral wall, a convex lateral wall, and two straight end walls that are more or less perpendicular to the top and bottom surfaces. One of the end walls of the cage includes a hole oriented toward the centre of the cage and intended to receive a rod of an instrument for insertion of the cage between the vertebrae. This intersomatic cage has the disadvantage of being in osseous tissue and therefore, as mentioned previously, of being capable of causing illness in the event of imperfect sterilisation. This cage may also have the disadvantage of eventually not being sufficiently solid to reliably take the stresses which will be applied to it when implanted in the disc space. Furthermore, this cage has the disadvantage of having a hole oriented toward the centre of the cage and in particular toward the centre of the concave surface, the result of which is to make the cage even more fragile. Moreover, the axis defined by this hole forms an angle, in relation to axis parallel to a tangent to one of the concave and convex surfaces, that is too large to allow to an instrument for insertion of the cage between the vertebrae to fit onto the cage in an orientation that is more or less parallel to a tangent to one of the concave and convex surfaces. Thus, the orientation of the hole does not conform to the general curvature of the cage obtained by its convex and concave surfaces and does not allow an effective thrust to be applied to the cage on its axis of curvature. The cage, which is made fragile by this hole, is therefore in danger of breaking when pressure has to be applied at an angle that is too large in relation to the axis of curvature of the cage, which therefore proves difficult to implant by the transforaminal approach. Finally, withdrawal of the instrument inserted into the hole proves to be difficult due to the unsuitable orientation of the latter.

In this context, it is of interest to propose an intersomatic cage, preferably in a solid and sterile material, that has a shape and dimensions that make it suitable to be implanted through the transforaminal approach without an excessively large lesion of the articular processes, and having resources to fit onto an instrument for insertion of the cage between the vertebrae, with an orientation that conforms to the general shape of the cage. It is also of interest to propose an instrument for implanting the cage, and which is designed for the shapes and dimensions of the cage, allowing easy implantation of the cage between the vertebrae. Also known from prior art are previous designs of instruments for the implantation of intersomatic cages that have at least one rod designed to be inserted into a hole in the cage in order to hold the latter during passage through the foramen. However some of these instruments known from prior art require an ablation of at least one part of the articular processes impeding access to the foramen when the cage and the instrument have excessively large dimensions. Moreover, the transforaminal approach is relatively obstructed and is not perfectly straight. It is therefore desirable that the instrument should have an elbow (a curved or angled portion) at the end holding the cage. Some instruments known from prior art have dimensions that are small enough not to necessitate ablation of the articular processes, and some of these instruments have an angled portion that allows one to bypass the structure obstructing access to the disc space, but the rod designed to hold the cage, as well as the hole of the cage in which this rod is designed to be inserted, have an orientation that it not very compatible with the optimal thrust axis allowing insertion of the cage between the vertebrae and not very compatible with easy withdrawal of the rod when the cage has been implanted. It is therefore desirable to propose an instrument whose shape and dimensions are suitable for insertion using the transforaminal approach, having an angled portion to bypass the structures obstructing access to the disc space and having a rod designed to be inserted into a hole in the cage with an orientation that is optimal in order to facilitate the implantation of the cage between the vertebrae, and then withdrawal of the instrument.

SUMMARY

This present invention has as its objective to circumvent some disadvantages of the previous designs by proposing an intersomatic cage for an intervertebral fusion graft of suitable shape and of limited dimensions to be implanted through the transforaminal approach while also having adequate robustness to effectively maintain a disc space that allows the growth of the graft.

This objective is met by a transforaminal intersomatic cage for an intervertebral fusion graft having a body in the shape of a circular arc, comprising a lateral concave surface, a lateral convex surface, a straight upper surface, a straight lower surface and an end wall with at least one hole, called the end hole, designed to receive a rod of an instrument for the implantation of a cage between the vertebrae, wherein:
   the end hole has an orientation that is more or less tangential to the circular arc described by the body;
   the extremity opposite to the end wall of the body includes a return part extending the body toward the centre of the circle on which the circular arc described by the body lies.

According to another feature, the end wall includes at least one recess designed to receive at least one pin of a cage implantation instrument.

According to another feature, the return part includes at least one hole, called the return hole, whose orientation is more or less tangential to a circular arc defined by the concave surface of the body and designed to receive at least one end portion of a cage implantation instrument.

According to another feature, the fitting together of the end hole, the recess and the return hole with, respectively, the rod, the pin and the end portion of the cage implantation instrument ensures a good grip on the cage by the instrument when one end of the rod is placed in the end hole, and facilitates the implantation of the cage, with the rod sliding in the instrument so that it can be removed from the end hole and allow freeing of the cage and withdrawal of the instrument.

According to another feature, at least one of the upper and lower surfaces of the body is endowed with serrations that oppose the movement of the cage in relation to the adjacent vertebrae between which it is implanted.

According to another feature, the return part includes upper and lower surfaces extending, respectively, the upper and lower surfaces of the body, with at least one of these upper and lower surfaces of the return part also being equipped with serrations that oppose the movement of the cage.

According to another feature, the return part includes upper and lower surfaces extending, respectively, the upper and lower surfaces of the body, with at least one of these upper and lower surfaces of the return part having at least one chamfer facilitating the insertion of the cage into the disc space.

According to another feature, the extremities of the circular arc described by the body define a longitudinal axis of the cage, with at least one part of the serrations being oriented parallel to this longitudinal axis of the cage.

According to another feature, the extremities of the circular arc described by the body define a longitudinal axis of the cage, with at least one part of the serrations being oriented perpendicularly to this longitudinal axis of the cage.

According to another feature, the extremities of the circular arc described by the body define a longitudinal axis of the cage, with at least one part of the serration having the shape of chevrons centred on an axis perpendicular to this longitudinal axis of the cage.

According to another feature, the extremities of the circular arc described by the body define a longitudinal axis of the cage, with at least one part of the serrations describing concentric circular arcs each having, together with the circular arc described by the body, an axial symmetry whose axis of symmetry is parallel to this longitudinal axis of the cage.

According to another feature, at least one part of the serrations are oriented parallel to radii defined by the circle on which the circular arc described by the body lies.

According to another feature, the serrations present on a given surface of the cage have the same orientation.

According to another feature, the serrations present on a given surface of the cage do not have the same orientation.

According to another feature, the serrations present on two opposite surfaces of the cage have the same orientation.

According to another feature, the serrations present on two opposite surfaces of the cage do not have the same orientation.

According to another feature, the body includes at least one radio-opaque marker allowing the cage to be viewed by x-ray.

Another objective of this present invention is to propose an instrument for implanting an intersomatic cage between the vertebrae, facilitating access to the disc space and allowing a good grip to be obtained on the cage.

This objective is met by an instrument for the implantation of a transforaminal intersomatic cage for an intervertebral fusion graft having a body in the shape of a circular arc, comprising a lateral concave surface, a lateral convex surface, a straight upper surface, a straight lower surface, and an end wall having at least one hole, called the end hole, designed to receive one end of a rod of the instrument, with the end hole having an orientation that is more or less tangential to the circular arc described by the body, wherein said instrument comprises an extremity for gripping the cage, called the gripping end, and an extremity for manipulating the instrument, called the handling end, wherein:
   the gripping end comprises at least one tube, called the guide tube onto one end of which is mounted, on one edge, a spatula, called the support spatula, in a circular arc, designed to at least partially fit onto the circular arc described by the body of the cage.
   the guide tube comprising, at the base of the support spatula, an opening through which one end of the rod, mounted to slide in the guide tube, has a shape and dimensions making it suitable to be inserted into the end hole of the cage, so as to allow the cage to be gripped.

According to another feature, the rod extends up to the vicinity of the handling end of the instrument.

According to another feature, the rod includes at least one button projecting through a groove on at least one edge of the instrument, where this button allows the rod to be slid and its position to be adjusted in relation to the opening present at the end of the guide tube holding the support spatula.

According to another feature, the guide tube includes, at the end on which the support spatula is mounted but on the opposite edge, at least one pin whose shape and dimensions are suitable to fit onto at least one recess present on the end wall of the cage.

According to another feature, the support spatula includes, at the end opposite to the guide tube, at least one end portion whose shape and dimensions make it suitable to be inserted into at least one hole, called the return hole, present on a return part extending the body of the cage toward the centre of the circle on which the circular arc defined by this body lies, at the end opposite to the end wall of the body, this return hole having an orientation that is more or less tangential to a circular arc defined by the concave surface of the body.

According to another feature, the fitting together of the rod, the pin and the end portion of the cage implantation instrument with, respectively, the end hole, the recess and the return hole of the cage, ensures a good grip on the cave by the instrument when one end of the rod is placed in the end hole, and facilitates the implantation of the cage, with the rod to slide in the guide tube allowing withdrawal of the rod from the hole and freeing of the cage, and facilitating the withdrawal of the instrument once the cage has been implanted.

According to another feature, the guide tube includes, at the end opposite to that holding the support spatula, a mobile portion that pivots in relation to a tube, called the aiming tube, extending up close to the handling end of the instrument, said mobile portion pivoting in at least one direction that is more or less parallel to the orientation of the circular arc defined by the support spatula.

According to another feature, the mobile portion and the aiming tube form a ball and socket connection, one of them having one end in the form of a sphere and the other having a hollow end forming a spherical recess whose shape and dimensions are complementary to those of this sphere.

According to another feature, at least the edge of the spherical recess located on the same side of the instrument as the support spatula, in the ball and socket connection formed by the mobile portion and the aiming tube, encompasses the sphere to a lesser extent than the other edges of this recess, so as to allow pivoting at least in a direction that is more or less parallel to the orientation of the circular arc defined by the support spatula.

According to another feature, the rod is flexible and traverses the ball and socket connection at its centre, the sphere having a channel at its centre to allow the rod to slide, where this channel has a hollowed portion at least on its edge located on the same side of the instrument as the support spatula, so as to allow the rod to slide through the ball and socket connection even when the instrument is in its angled position due to pivoting of the hall and socket connection in a direction that is more or less parallel to the orientation of the circular arc defined by the support spatula.

According to another feature, a locking tube is screwed onto the aiming tube and includes a locking ring that allows the locking tube to be screwed in, so that screwing in and unscrewing results in forward and reverse motion of the locking tube in relation to the aiming tube, the forward motion of the locking tube resulting in bringing the locking tube into contact with the mobile portion and, as a consequence, preventing the pivoting of the mobile portion of the guide tube in relation to the aiming tube, to any angle between the guide tube and the aiming tube.

According to another feature, the mobile portion that pivots in relation to the aiming tube includes at least one serration which is used to obtain a given angle between the guide tube and the aiming tube, where the maximum angle in the presence of this serration is greater than in its absence because of the presence of the locking tube.

According to another feature, at least one edge of one end of the locking tube locks into the serration, when the guide tube forms a given angle with the aiming tube, so as to prevent pivoting and to maintain the instrument in at least one position, until it is totally immobilised by screwing in the locking tube.

According to another feature, the handling end of the instrument is fitted with a handle allowing the manipulation of the instrument and facilitating the implantation of the cage between the vertebrae, by allowing effective thrust to be applied to the instrument.

Another objective of the preset invention is to propose a method for implanting a transforaminal intersomatic cage according to the invention into the disc space with an instrument according to the invention.

This objective is reached by a method for implanting a transforaminal intersomatic cage for an intervertebral fusion graft having a body in the shape of a circular arc, comprising a lateral concave surface, a lateral convex surface, a straight upper surface, a straight lower surface and an end wall with at least one hole, called the end hole, having an orientation that is more or less tangential to the circular arc described by the body and designed to receive a rod of an instrument for the implantation of a cage between the vertebrae, the extremity opposite to the end wall of the body including a return part extending the body toward the centre of the circle on which the circular arc described by the body lies, said return part including at least one hole, called the return hole, whose orientation is more or less tangential to a circular arc defined by the concave surface of the body and designed to receive at least one end portion of a cage implantation instrument, said method comprising a step of insertion of the cage in the disc space with an instrument comprising an extremity for gripping the cage, called the gripping end, and an extremity for manipulating the instrument, called the handling end, said gripping end comprising at least one tube, called the guide tube onto one end of which is mounted, on one edge, a spatula, called the support spatula, in a circular arc, designed to at least partially fit onto the circular arc described by the body of the cage, said spatula including, at the end opposite to the guide tube, at least one end portion whose shape and dimensions make it suitable to be inserted into the return hole and said guide tube comprising, at the base of the support spatula, an opening through which one end of the rod, mounted to slide in the guide tube, has a shape and dimensions making it suitable to be inserted into the end hole of the cage, said method comprising the following steps:
  incising the skin and muscles laterally to the vertebral column, incising the annulus, removing the nucleus and clearing the disc space, inserting the end portion of the spatula into the return hole of the cage, moving the circular arc of the body in relation to the spatula and locking the cage onto the instrument by sliding the rod until it enters into the end hole, impacting the cage in the disc space, in a circular movement, releasing the cage from the instrument by sliding the rod until it exits from the end hole and removing the instrument, suturing the annulus and the skin.

According to another feature, the step of impacting the cage in the disc space is preceded or accompanied by a step of articulating a mobile portion at a distal end of the instrument to find the most appropriate angle for engagement of the cage in the disc space, said step of articulating the mobile portion being followed by a step of locking the mobile portion at the desired angle by screwing a locking tube preventing the pivoting of the mobile portion.

According to another feature, the step of impacting the cage in the disc space is followed by a step of checking the position and orientation of the cage in the disc space by applying x-ray detecting at least one radio-opaque marker present in the body of the cage, said step of checking being, if necessary, followed by a step of adjusting the position and/or orientation of the cage in the disc space, prior to release from the instrument.

According to another feature, the step of inserting the end portion of the spatula into the return hole of the cage and moving the circular arc of the body in relation to the spatula is followed, when the guide tube of the instrument includes, at the end on which the support spatula is mounted but on the opposite edge, a pin whose shape and dimensions are suitable to fit onto at least one recess present on the end wall of the cage, by a step of locking said pin into said recess, prior to locking the cage onto the instrument by sliding the rod until it enters into the end hole.

According to another feature, the step of impacting the cage in the disc space is preceded by a step of distraction of the adjacent vertebrae by tools of known types, in order to facilitate the access to the disc space

BRIEF DESCRIPTION OF THE DRAWINGS

Other features and advantages of this present invention will appear more clearly on reading the description that follows, provided with reference to the appended drawings, in which.

DETAILED DESCRIPTION OF THE EMBODIMENTS

Figure 1A:
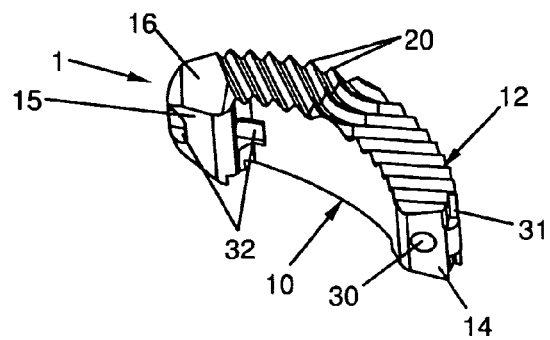
FIGS. 1 A, 1 B, 1 C and 1 D are views in perspective of the intersomatic cage according to various embodiments of the invention.

This present invention concerns a transforaminal intersomatic cage for an intervertebral fusion graft. This cage is used to maintain a disc space that is sufficient to allow a graft to be inserted into the disc space in order to grow and to allow an osseous fusion (arthrodesis) of the adjacent vertebrae. This cage is called transforaminal since it is particularly suitable to be implanted through the transforaminal approach, although it can also be implanted by any approach to suit the convenience of the surgeon responsible for the implantation. In a manner which is already known, this intersomatic cage has a body (1) in the shape of a circular arc having a lateral concave surface (10), a lateral convex surface (11), a straight upper surface (12), and a straight lower surface (13). The body (1) therefore has more or less the shape of a banana or simple bracket, and therefore does indeed describe a circular arc.

This circular arc shape of the cage according to various embodiments of the invention is particularly well-matched to the shape of the edges of the vertebral plates, which allows the cage to be positioned in the vicinity of the periphery of the vertebral plates, that is to say on their most solid portion. A cage according to various embodiments the invention will therefore be implanted at the level of the anterior peripheral portion of the vertebral plates, for example. This positioning of the cage close to the edges of the vertebral plates also enables to obtain a large initial surface for an osseous graft or a substitute. At one of the extremities of the body (1), the cage includes an end wall (14) having at least one hole (30), called the end hole, designed to receive a rod (53) of an instrument (5) for implantation of the cage between the vertebrae.

In a particularly advantageous embodiment of the cage according to the invention, the end hole (30) has an orientation that is more or less tangential to the circular arc described by the body (1). This orientation of the end hole (30) tangentially to the circular arc described by the body (1) facilitates the thrusting of the cage by the cage implantation instrument (5) and facilitates the insertion and withdrawal of the rod (53) of this instrument (5), respectively, into and out of the end hole (30). Moreover, this end wall (14) includes at least one recess (31) designed to receive at least one pin (54) of a cage implantation instrument (5). This recess (31) is used to provide an additional surface for the gripping of the cage by the instrument. It can consist of a simple shoulder or a recess of more complex shape such as, for example, a recess with a groove in which a serration of the pin (54) (thus having the shape of a spur, for example) of the instrument (5) can be locked.

In a particularly advantageous embodiment of the cage according to the invention, the extremity opposite to the end wall (14) of the body (1) includes a return part (15) extending the body (1) toward the centre of the circle on which the circular are described by the body (1) lies. This return part provides better stability of the intersomatic cage between the vertebrae without increasing its dimensions excessively. This return part is used to prevent the intersomatic cage from tilting to one of its sides under the effect of the stresses to which it is subjected when implanted between two vertebrae of a patient. Moreover, this return part (15) includes at least one hole (32), called the return hole, whose orientation is more or less tangential to a circular arc defined by the concave surface (10) of the body (1) and designed to receive at least one end portion (55) of a cage implantation instrument (5). Thus, the instrument (5) can include a spatula (56) having a shape complementary to that of the circular arc described by the body. This spatula (56) thus hugs the shape of the cage by fitting its body (1). At one end of the spatula (56), an end portion (55) can be designed for insertion into this return hole (32). The fitting together of the end hole (30), the recess (31) and the return hole (32) with the rod (53), the pin (54) and the end portion (55) of the cage implantation instrument (5) respectively, ensures a good grip on the cage by the instrument (5) when one end of the rod (53) is placed in the end hole (30). This complete gripping of the cage up to the most distal end facilitates the implantation of the cage by providing good stability of the cage at the end of the instrument (5). This good stability is also particularly important in the case of implantation through the transforaminal approach. The rod (53) is designed to slide in the instrument (5) so that it can be withdrawn from the end hole (30) and to allow freeing of the cage and withdrawal of the instrument (5).

Figure 1B:
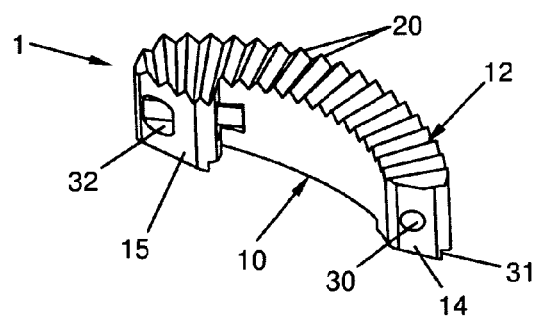
Figure 1C:
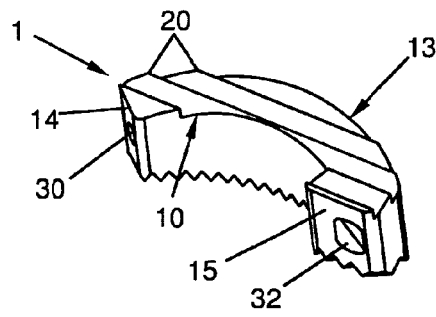
Figure 1D:
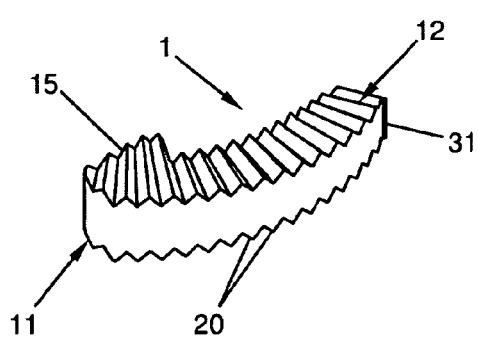

In a manner which is already known, at least one of the upper and lower surfaces of the body (1) is equipped with serrations (20) that oppose the movement of the cage in relation to the adjacent vertebrae between which it is implanted. The invention provides for different possible orientations of the serrations (20). In an advantageous manner, in one embodiment of the invention, the serrations (20) present on two opposite surfaces of the cage may not have the same orientation, so as to oppose the movement of the cage in different directions for each of the faces, as can be seen particularly in FIGS. 1A to 1C. In another embodiment, the serrations (20) present on two opposite surfaces of the cage will have the same orientation, as can be seen particularly in FIG. 1D. Likewise, serrations (20) present on one surface of the cage can have an orientation that is different from other serrations located on the same surface. Conversely, all the serrations (20) present on a given surface of the cage can have the same orientation. Depending on the embodiment, the intersomatic cage can therefore include any combination of these orientations on all or part of either of its surfaces. The extremities of the circular arc described by the body (1) define a longitudinal axis of the cage. The cage has larger dimensions on this longitudinal axis than on the axis perpendicular to it. This longitudinal axis will allow the different possible orientations of the serrations to be defined. Thus in one embodiment, at least one part of the serrations (20) can be oriented parallel, as can be seen particularly in FIG. 1C, or perpendicular to this longitudinal axis of the cage. In another embodiment, they can be oriented so as to form an angle of between 0 and 90 degrees in relation to this longitudinal axis of the cage. In another embodiment, at least one part of the serrations (20) can describe chevrons that are centred in relation to an axis perpendicular to this longitudinal axis, as can be seen particularly in FIG. 1A. In another embodiment, at least one part of the serrations (20) can describe concentric circular arcs, each with, in relation to the circular arc described by the body (1), an axial symmetry whose axis of symmetry is parallel to this longitudinal axis of the cage. In another embodiment, at least one part of the serrations (20) will be oriented parallel to radii defined by the circle on which the circular arc described by the body lies (1), as can be seen particularly in FIGS. 1 B and 1 D.

Furthermore, the return part (15) includes upper and lower surfaces extending the upper and lower surfaces respectively of the body (1). In one embodiment, at least one of these upper and lower surfaces of the return part (15) can also be equipped with serrations (20) that oppose the movement of the cage. In another embodiment, at least one of these upper and lower surfaces of the return part (15) can include at least one chamfer (16) facilitating the insertion of the cage in the disc space, as can be seen particularly in FIG. 1A.

This present invention also concerns an instrument (5) for the implantation of an intersomatic cage between the vertebrae. This instrument according to the invention is particularly suitable for implantation, through the transforaminal approach, of an intersomatic cage for an intervertebral fusion graft, although it could naturally be used for any approach that is convenient for the surgeon responsible for the implantation. The instrument (5) is designed to be particularly suitable for use in combination with the intersomatic cage described previously. The instrument (5) according to an embodiment of the invention includes an extremity for gripping the cage allowing the cage to be held at the end of the instrument and called the gripping end. The extremity of the instrument opposite its gripping end allows the manipulation of the instrument by the surgeon and is called the handling end. The gripping end of the instrument (5) includes at least one tube (52), called the guide tube. At the extremity of this guide tube (52), on one edge of the latter, is mounted a spatula (56), called the support spatula. This spatula (56) has the shape of a circular arc, designed to at least partially fit onto the circular arc described by the body (1) of the cage. By hugging the shape of the body (1), this spatula provides the cage with solidity. The spatula will therefore protect the cage in particular against impact, to which it is sometimes less resistant than to pressures. At the base of the support spatula (56), the guide tube (52) includes an opening through which one end of the rod (53) passes to fit into the end hole (30) of the cage. This rod (53) is mounted to slide in the guide tube (52) and has a shape and dimensions that make it suitable to be inserted into the end hole (30) of the cage, so as to allow the cage to be gripped. In one embodiment, this rod (53) extends up to the vicinity of the handling end of the instrument (5). The rod (53) includes at least one button (61) projecting through a groove (610) on at least one edge of the instrument (5), this button (61) allowing the rod to be slid (53) and its position to be adjusted in relation to the opening present at the end of the guide tube (52) holding the support spatula (56). This button will preferably be located at the extremity of the rod (53) and, according to the embodiment, can therefore be located close to the handling end of the instrument (5) or anywhere on the instrument, although it would obviously be more practical, in principle, that it should be close to the handling end.

In one embodiment, the guide tube (52), at the end on which the support spatula is mounted (56) but on the opposite edge, includes at least one pin (54) whose shape and dimensions are suitable to fit onto at least one recess (31) present on the end wall (14) of the cage. This embodiment is particularly suitable for the one of the embodiments of the cage presented above and improves the quality of the grip on the cage by the instrument (5).

In one embodiment, the support spatula (56), at the end opposite to the guide tube (52), includes at least one end portion (55) whose shape and dimensions make it suitable to be inserted into at least one hole (32), called the return hole, present on a return part (15) of the cage. This embodiment is particularly suitable for the one of the embodiments of the cage in which a return part (15) extends the body (1) toward the centre of the circle on which the circular arc described by the body (1) lies. Since this return hole (32) has an orientation that is more or less tangential to a circular arc defined by the concave surface (10) of the body (1), the end portion (55) at the end of the spatula (56) in a circular arc will therefore have a shape that is particularly suitable to fit into the return hole (32). In one embodiment that combines the resources for fitting together the instrument and the cage, described above, with the fitting together of the rod (53), the pin (54) and the end portion (55) of the cage implantation instrument (5) to the end hole (30), the recess (31) and the return hole (32) respectively of the cage, ensures a good grip on the cage by the instrument (5) when one end of the rod (53) is placed in the end hole (30), and facilitates the implantation of the cage.

Figure 3A:
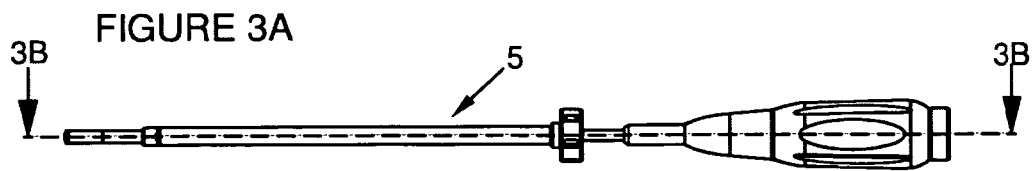
FIG. 3A provides a top view of one embodiment of the instrument for implanting an intersomatic cage with a plane section 3B-3B, with FIG. 3B showing a view in section according to axis 3B-3B of this embodiment of the insertion instrument, and FIGS. 3C and 3D showing the detail of the portions indicated, respectively, by circles 3C and 3D in FIG. 3B.
Figure 3B:
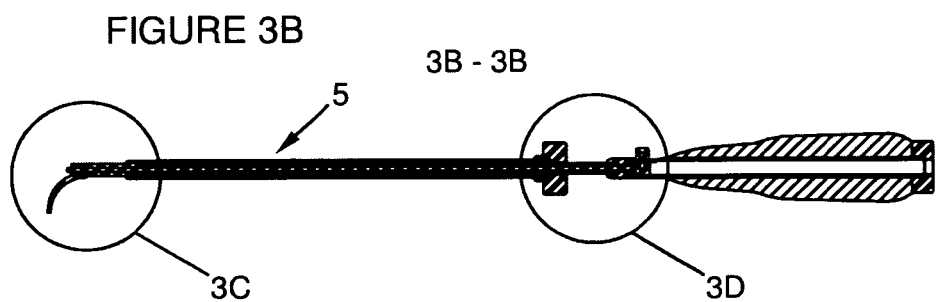
Figure 3C:
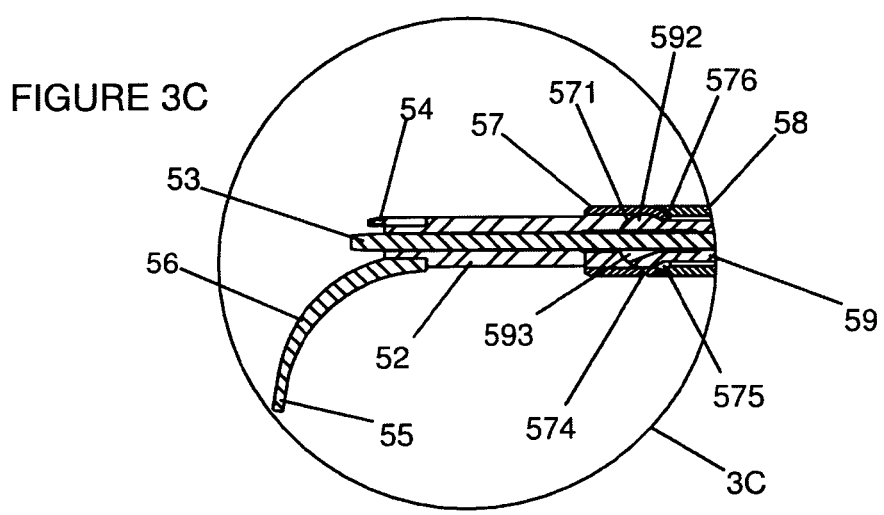
Figure 3D:
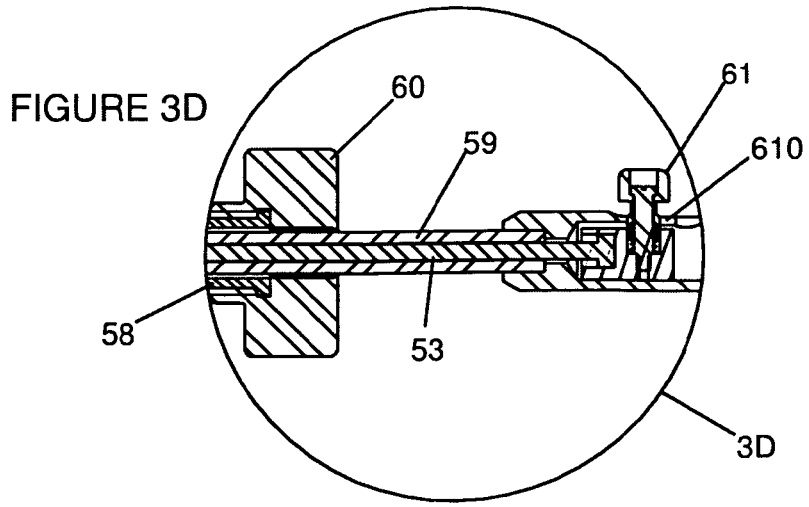
Figure 4A:
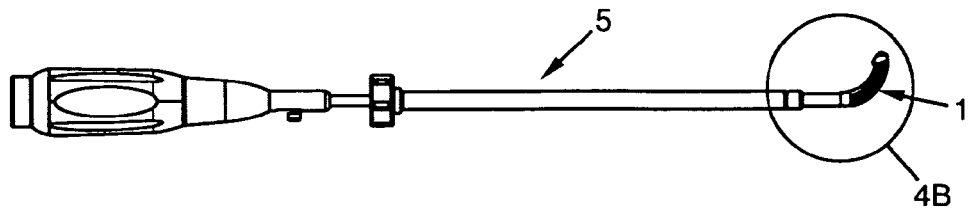
FIG. 4A provides a view in profile of one embodiment of the instrument for implanting an intersomatic cage with a method for insertion of the intersomatic cage held at the gripping end of the instrument, with FIG. 4B showing the detail of the portion indicated by circle 4B in FIG. 4A, and FIG. 4C showing a top view of this embodiment of the instrument holding the intersomatic cage, with a plane section 4D-4D, where FIG. 4D provides a view in section according to axis 4D-4D of this embodiment.
Figure 4B:
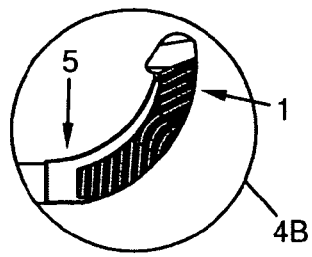
FIG. 4E shows the detail of the portion indicated by circle 4E in FIG. 4D.
Figure 4C:
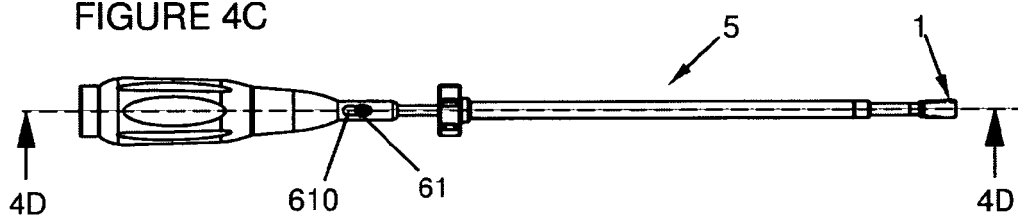
Figure 4D:
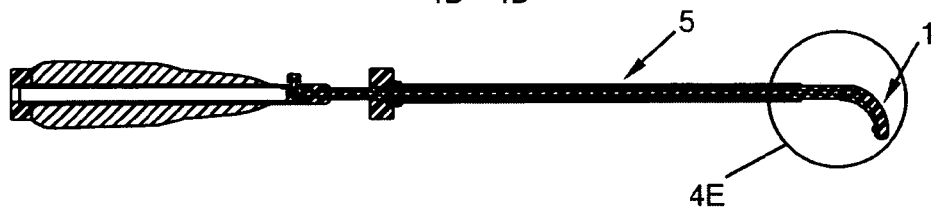
Figure 4E:
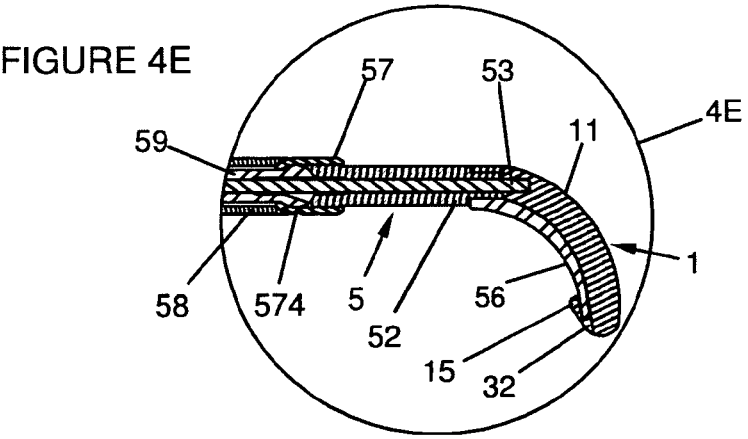

In a particularly advantageous embodiment and suitable for the transforaminal approach, the guide tube (52), at the end opposite to that holding the support spatula (56), includes a mobile portion (57) that pivots in relation to a tube (59), called the aiming tube, extending up close to the handling end of the instrument (5). This mobile portion (57) pivots in at least one direction that is more or less parallel to the orientation of the circular arc defined by the support spatula (56). As can be seen particularly in FIG. 3C, the mobile portion (57) and the aiming tube (59) together can form a ball and socket connection (or swivel link), one of them having one end in the form of a ball or sphere (592) and the other having a hollow end forming a socket, called spherical recess (571), whose shape and dimensions are complementary to those of this sphere. In the embodiment illustrated in FIG. 3C, one end of the aiming tube (59) has a shape of sphere (592) and the corresponding end of the guide tube (52) forms a spherical recess. In one embodiment of the invention, at least the edge (575) of the spherical recess (571) located on the same side of the instrument (5) as the support spatula (56), in the ball and socket connection formed by the mobile portion (57) and the aiming tube (59), encompasses the sphere to a lesser extent than the other edges (576) of this recess (571), so as to allow pivoting at least in a direction that is more or less parallel to the orientation of the circular arc defined by the support spatula (56).

Figure 2A:
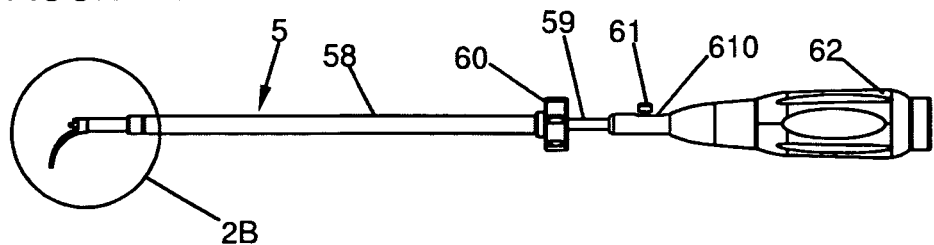
FIGS. 2A and 2C are views in profile of one embodiment of the instrument for implanting intersomatic cage between the vertebrae, with the gripping end of the instrument in position, respectively straight and angled, with FIGS. 2B and 2D showing the detail of the portions indicated by circles 2B and 2D respectively in FIGS. 2A and 2C respectively.
Figure 2B:
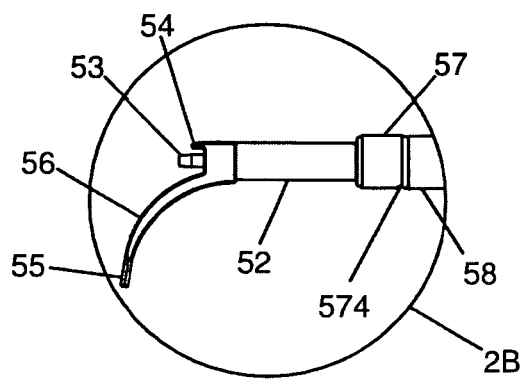
Figure 2C:
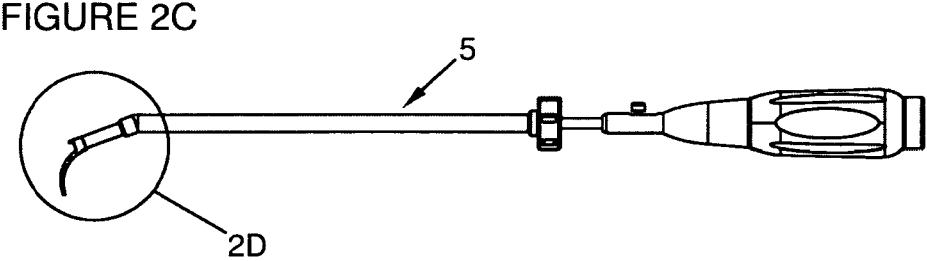
Figure 2D:
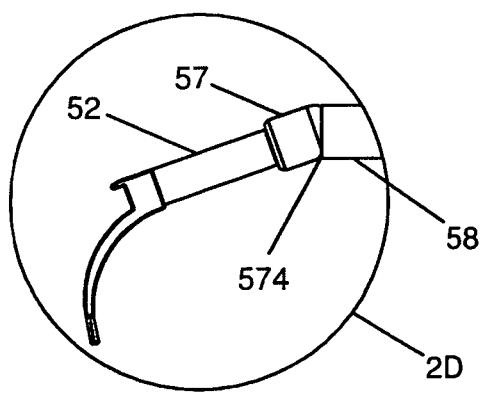

In one embodiment, the rod (53) is flexible, and traverses the ball and socket connection at its centre. The sphere (592) then has a channel at its centre to allow the rod to slide (53). This channel will be hollowed out at least on its edge located on the same side of the instrument (5) as the support spatula (56). Thus, the channel will include a hollowed out portion (593) allowing the rod (53) to slide through the ball and socket connection even when the instrument (5) is in its angled position due to pivoting of the ball and socket connection, as illustrated in FIGS. 2C and 2D.

In one embodiment, a locking tube (58) is screwed onto the aiming tube (59) and includes a locking ring (60) that allows the locking tube to be screwed in (58). Screwing-in and unscrewing allows the forward and backward motion of the locking tube (58) in relation to the aiming tube (59). The forward motion of the locking tube (58) results naturally in bringing the locking tube (58) into contact with the mobile portion (57) and, as a consequence, prevents the pivoting of the mobile portion (57). Thus, the guide tube (52) can be locked in relation to the aiming tube (59), at any angle between the guide tube (52) and the aiming tube (59). The mobile portion (57) that pivots in relation to the aiming tube (59) can also, in one embodiment, include at least one serration (574), particularly visible in FIG. 3C. The presence of this serration (574) allows pivoting of the mobile portion (57) through a larger amplitude than if the mobile portion entered directly into contact with the locking tube (58). This serration (574) allows to obtain a particular angle formed by the angled portion between the support tube (52) and the aiming tube (59). Moreover, in one embodiment, this serration (574) can be designed so that when the guide tube (52) forms a given angle with the aiming tube (59), one edge of one end of the locking tube (58) locks into this serration (574), as illustrated in FIGS. 2A to 2D. This serration (574) is therefore used to stop the pivoting and to maintain the instrument in at least one position until it is totally immobilised by screwing-in of the locking tube (58).

In a manner which is already known, the handling end of the instrument (5) can naturally be fitted with a handle (62) allowing the manipulation of the instrument (5) and facilitating the implantation of the cage between the vertebrae by allowing effective thrust to be applied to the instrument (5).

As mentioned previously, the intersomatic cage and the instrument according to this present invention are particularly suitable for implantation of the cage between two adjacent vertebrae using the transforaminal approach. This implantation can be performed as described below, although other procedural variants can naturally exist, and the surgeon can naturally adapt the technique described here at his convenience, in accordance with any changes in the techniques employed conventionally for example. In particular, this present invention can be used in combination with osseous anchor implants, connected together by immobilising bars, allowing the movement of the two adjacent vertebrae, between which the cage is designed to be inserted, to be eliminated or limited. These osseous anchor implants can consist, for example, of those described in the international patent applications submitted by this present applicant and published under the numbers WO02/080788(A1), WO03/049629(A1) and WO2005/020829(A1) or by any other type of resources for immobilisation of the adjacent vertebrae. The procedure relating to the joining of the adjacent vertebrae is specific to the resources used to immobilise the adjacent vertebrae and therefore need not be described here.

Only the procedure used during an implantation through the transforaminal approach will be detailed here, the implantation by other approaches being relatively similar but easier, in particular because of the fact that the transforaminal approach needs to bypass the articular processes. The procedure for implantation through the transforaminal approach begins naturally by at least one incision laterally to the axis of the vertebral column. Preferably, two intermuscular incisions will be made, along a path that is well known to the professional surgeon for example, as described by Dr Wiltse. According to the size of the cage chosen and/or according to the space between the two vertebrae, a resection, at least partial, of the articular processes can be effected in order to improve access to the foramen and to the disc space. These articular processes will then preferably be resected laterally, on the side for insertion of the cage. If an intra-articular graft is desired, an opening and an avivement (withdrawal of the cartilage) of the articular processes, at least on one side but possibly on both sides, will allow the insertion of at least one intra-articular graft. The insertion of the osseous anchor implants designed to immobilise the two adjacent vertebrae can be effected at this stage of the procedure. These osseous anchor implants screwed into each of the adjacent vertebrae and connected together by a bar, here allow a first posterior distraction in order to facilitate access to the disc space. A tool of known type such as a nerve root retractor (or root spreader) can be used to protect the roots of the vertebrae. A lateral incision in the external layer of the annulus, between the transverse articular processes for example, will provide access to the disc space. In a manner which is already familiar, the formation of an open flap, held by suspension ties for example, will facilitate the following operations. Then the surgeon will proceed to the complete removal of the nucleus and of the internal layers of the annulus. Different tools of known types, such as an angled disc clamp, curettes and rasps (straight and angled) will be used at this stage to prepare the disc space and withdraw the cartilage from the vertebral plates without damaging or weakening it.

At this stage of the procedure, the surgeon will have Cleared access to the disc space. The osseous anchor implants will allow the surgeon to spread the vertebrae so as to facilitate insertion of the cage. For example, the surgeon will use osseous anchor implants screwed into the vertebrae and connected together by a bar parallel to the axis of the vertebral column. The osseous anchor implants generally include screws driven into the vertebrae and defining a longitudinal securing axis. At this stage, these longitudinal axes of the osseous anchor implant are not parallel to each other but cross in front of the vertebral column. Together with the axis of the bar, these axes form an inverted capital A. The surgeon will then adjust the spread of the osseous anchor implants. To this end, the surgeon can position spreader tubes on the heads of the osseous anchor implants in order to spread these as much as possible, and will then screw in the head of these osseous anchor resources on the bar to fix their position along the bar parallel to the axis of the vertebral column. The osseous anchor implants thus implanted and held securely on the bar will allow an anterior distraction to be performed. The surgeon applies pressure to the spreader tubes so as to move them toward each other, which tends to open the inverted capital A at its base, so that it becomes a capital H. This operation can possibly be repeated several times by unscrewing the heads of the osseous anchor implants from the bar and separating the spreader tubes to spread the heads and then screwing in the heads of the implants and drawing together the spreader tubes to spread the feet of the capital H, thus opening the disc at the front. This anterior opening of the disc space can be accompanied by an adjustment of the lordosis.

The surgeon will then proceed to the choice of the cage to be implanted, using trial cages with the same dimensions as the cages designed to be implanted. A trial cage is placed on the instrument (5) and is then impacted into the disc space. Impaction should be effected without excessive force in order not to weaken (damage) the vertebral plates. The trial cage is removed using a tool of known type such as an extraction masselotte (or extractor or removal masselotte or bobweight), and this operation can be repeated until a cage of satisfactory size has been found.

The definitive cage can then be placed on the implantation instrument (5) by inserting the end portion (55) of the spatula (56) into the return hole (32) of the cage and moving the circular arc of the body (1) in relation to the spatula (56) until the pin (54) locks into the recess (31) of the end wall (14). The cage is than locked onto the instrument (5) by means of the sliding rod (53) which enters into the end hole (30). Articulation of the instrument at its distal part by means of the mobile portion (57) allows the most appropriate angle to be found for engagement of the cage in the intersomatic space. The angle can be locked by the screwing in the locking tube (58) using the threaded ring (60) for example by means of a tool of known type such as a pin wrench. The cage thus held on the instrument and oriented in an optimal manner can then be impacted between the vertebrae. The cage will preferably be impacted as anteriorly as possible, in a circular movement. In order to optimise the positioning of the cage, the angle of the articulation formed by the mobile part (57) can be adjusted during impaction, taking care to correctly lock this angle by means of the locking ring (60). The position and the orientation of the cage in the intersomatic disc space can then be verified by means of an x-ray appliance of known type, such as a brightness amplifier for example. In fact, in one embodiment the cage includes at least one radio-opaque marker which will be detected by the brightness amplifier. The surgeon can then adjust the positioning of the cage according to the position and the orientation of the marker or markers. When the cage has been correctly implanted, it will be released from the instrument (5) by moving the sliding rod (53) in the direction of the handling end. The surgeon then only has to position the osseous graft(s) or substitute(s) between the cage (preferably placed at the level of the anterior edges of the vertebral plates) and the medullary cavity. To this end, the surgeon will use a tool of known type, such as a spatula for example. The flap formed in the external layer of the annulus can then be re-closed and sutured, so as to maintain the graft in place. A graft, of the posterolateral type for example, can be effected at this stage in order to optimise the joining together of the vertebrae. Graft will be then placed on the transverse articular process for example. A redon drain can possibly then be put in place, and a subcutaneous suturing followed by a cutaneous suturing of the incisions will allow the surgical procedure to be finalised.

It should be obvious to people well versed in these techniques that this present invention allows embodiments in many other specific forms without the moving outside the scope of the invention as claimed. As a consequence, the present embodiments should be considered as illustrations only, but can be modified within the domain defined by the reach of the attached claims, and the invention must not be limited to the details given above.

The invention claimed is:

1. A combination comprising an intersomatic cage for an intervertebral fusion graft comprising an elongated body having proximal-most and distal-most ends and generally defining an arc extending between the proximal-most and distal-most ends, the body comprising a lateral concave surface having a first length extending from a point proximal to the proximal-most end to a point proximal to the distal-most end, a lateral convex surface, a substantially transverse upper surface, a substantially transverse lower surface, and an end wall disposed along the first proximal-most end of the body and comprising an end hole, and an instrument for the implantation of the intersomatic cage, the instrument comprising:

a gripping end for gripping the intersomatic cage;

a handling end for manipulating the instrument;

a guide tube extending between the gripping end and the handle, the guide tube having a central longitudinal axis along a central bore and an opening proximal to the gripping end;

a rod slidably disposable in the guide tube and comprising a retaining end configured to protrude from the opening and to penetrate the end hole; and an elongated support spatula generally defining an arc that is complementary to the arc defined by the body and that has a convex surface having a second length substantially the same as the first length.

2. The combination according to claim 1, wherein the rod extends substantially to the vicinity of the handling end of the instrument.

3. The combination according to claim 1, wherein the instrument comprises a button attached to the rod and a groove through which the button projects, the button being configured for sliding the rod to adjust the position of the retaining end of the rod in relation to the opening in the guide tube.

4. The combination according to claim 1, wherein the guide tube comprises a pin configured to engage a recess disposed on the end wall of the intersomatic cage.

5. The combination according to claim 1, wherein the spatula is extended by a tip configured for insertion into a retention receptacle disposed along the lateral concave surface of the cage body proximal to the distal-most end of the body and oriented toward the proximal-most end of the body.

6. The combination according to claim 5, wherein the guide tube comprises a pin configured to engage a recess disposed on the end wall of the intersomatic cage, the retaining end of the rod, the pin, and the tip of the spatula being configured to cooperate with, respectively, the end hole, the recess, and the retention receptacle, to secure a grip on the intersomatic cage by the implantation instrument, and to facilitate the withdrawal of the instrument following implantation of the intersomatic cage by removing the retaining end of the rod from the end hole.

7. The combination according to claim 5, wherein the spatula contacts the lateral concave surface of the intersomatic cage from the retention receptacle to the proximal-most end of the body.

8. The combination according to claim 1, further comprising an aiming tube that extends substantially to the vicinity of the handling end of the instrument, wherein the guide tube comprises a mobile portion that pivots in relation to the aiming tube at least in a primary pivot direction, the primary pivot direction lying substantially within a plane in which the arc defined by the support spatula lies, and the position of the mobile portion in relation to the aiming tube defining a pivot angle.

9. The combination according to claim 8, wherein one of the mobile portion or the aiming tube comprises a substantially spherical end, and the other of the mobile portion or the aiming tube comprises a recessed end having a shape and dimensions complementary to the shape and dimensions of the spherical end, the spherical end and the recessed end being configured, respectively, as a ball component and a socket component of a ball and socket connection.

10. The combination according to claim 9, wherein the socket component comprises opening edge portions, one of which portions is proximal to the support spatula and is configured to encompass the ball component less than the other opening edge portions to allow further pivoting of the mobile portion in relation to the aiming tube at least in the primary pivot direction.

11. The combination according to claim 9, wherein the rod is flexible and slidably transits the ball and socket connection through a channel located at the centre of the ball component and the socket component, the channel having a hollowed portion proximal to the support spatula, the hollowed portion configured to allow the rod to slide through the ball and socket connection even when the mobile portion is pivoted in relation to the aiming tube.

12. The combination according to claim 8, the instrument further comprising a lock slidably disposed along the aiming tube, the lock having a forward position and being configured to fix the mobile portion of the guide tube at a selected pivot angle when the lock is disposed in the forward position.

13. The combination according to claim 12, wherein the mobile portion comprises a serration configured to increase the maximum pivot angle at which the mobile portion of the guide tube can be fixed by the lock and to provide a pre-determined pivot angle.

14. The combination according to claim 13, wherein the serration is configured for engagement with the lock without disposing the lock in the forward position, said engagement establishing a pre-determined pivot angle and preventing pivoting of the mobile portion.

15. The combination according to claim 1, wherein the handling end of the instrument comprises a handle configured to allow the manipulation of the instrument and to facilitate the implantation of the intersomatic cage between the vertebrae.

16. A method for implanting an intersomatic cage for an intervertebral fusion graft into the disc space between adjacent vertebrae of a vertebral column, said disc space comprising a nucleus, said method comprising the steps of:
  acquiring an intersomatic cage for an intervertebral fusion graft comprising an elongated body having proximal-most and distal-most ends and generally defining an arc extending between the proximal-most and distal-most ends, the body comprising a lateral concave surface having a first length extending from a point proximal to the proximal-most end to a point proximal to the distal-most end, a lateral convex surface, a substantially transverse upper surface, a substantially transverse lower surface, and an end wall disposed along the proximal-most end of the body and comprising an end hole an instrument for the implantation of the intersomatic cage,
  acquiring an instrument comprising: a gripping end for gripping the intersomatic cage; a handling end for manipulating the instrument; a guide tube extending between the gripping end and the handle, the guide tube having a central longitudinal axis along a central bore and an opening proximal to the gripping end; a rod slidably disposable in the guide tube and comprising a retaining end configured to protrude from the opening and to penetrate the end hole; and an elongated support spatula generally defining an arc that is complementary to the arc defined by the body and that has a convex surface having a second length substantially the same as the first length;
  making an incision to access the vertebral column;
  inserting a tip of the spatula into a retention receptacle of the cage;
  disposing a convex spatula surface along the lateral concave surface of the cage;
  fixing the cage onto the instrument by inserting the retaining end of the rod into the end hole;
  disposing the cage in the disc space in an arcing movement;
  releasing the cage from the instrument by removing the retaining end of the rod from the end hole and removing the tip of the spatula from the retention receptacle of the cage;

removing the instrument from the disc space; and closing the incision.

17. A method according to claim 16, wherein the step of disposing the intersomatic cage in the disc space is preceded or accompanied by a step of articulating a mobile portion of the instrument to a selected angle, said step of articulating the mobile portion being followed by a step of locking the mobile portion at the selected angle.

18. A method according to claim 16, wherein the step of disposing the intersomatic cage in the disc space is followed by the steps of determining the position and orientation of the intersomatic cage in the disc space by detecting a radio-opaque marker comprised in the body of the intersomatic cage with x-rays and, if such position or orientation is improper, adjusting the position or orientation of the intersomatic cage in the disc space.

19. A method according to claim 16, wherein the steps of inserting the tip of the spatula into the retention receptacle of the intersomatic cage and disposing the convex spatula surface along the lateral concave surface of the cage are followed by, and the step of fixing the intersomatic cage onto the instrument by inserting the retaining end of the rod into the end hole is preceded by, a step of engaging a pin of the instrument with a recess disposed on the end wall of the intersomatic cage.

20. A method according to claim 16, wherein the step of disposing the intersomatic cage in the disc space is preceded by a step of distraction of the adjacent vertebrae.

\* \* \* \* \*